US006187978B1

(12) United States Patent
Rygas et al.

(10) Patent No.: US 6,187,978 B1
(45) Date of Patent: Feb. 13, 2001

(54) CONTINUOUS PROCESS FOR MANUFACTURING HALOGENATED COMPOUNDS

(75) Inventors: Tedeusz P. Rygas, Kanata (CA); Hsuch Sung Tung, Erie County, NY (US)

(73) Assignee: AlliedSignal Inc., Morristown, NJ (US)

( * ) Notice: Under 35 U.S.C. 154(b), the term of this patent shall be extended for 0 days.

(21) Appl. No.: 09/310,386

(22) Filed: May 12, 1999

(51) Int. Cl.⁷ .................................................... C07C 17/26
(52) U.S. Cl. ........................................... 570/257; 570/172
(58) Field of Search ..................................... 570/172, 257

(56) References Cited

U.S. PATENT DOCUMENTS 3,862,978 * 1/1975 Decker et al. ........................ 570/172
5,902,914   5/1999 Rygas et al. .

OTHER PUBLICATIONS

Kotora et al. "Selective Addition of Polyhalogenated Compounds to Chlorosubstituted Ethenes Catalyzed by a Copper Complex," React. Kinet. Catal. Lett. vol. 44, No. 2, 415–419 (1991).

Zhiryukina et al. Synthesis of Polychloroalkanes with Several Different Chlorine–Containing Groups, Translated from Izvestiya Akademii Nauk SSSR, Seriya Khimcheskaya, No. 1, 152–157 (1983).

Kotora et al. "Addition of Tetrachloromethane to Halogenated Ethenes Catalyzed by Transition Metal Complexes," *Journal of Molecular Catalysis,* 77 (1992) 51–60.

* cited by examiner

*Primary Examiner*—Alan Siegel
(74) *Attorney, Agent, or Firm*—Colleen D. Szuch; Marie L. Collazo

(57) ABSTRACT

A process for preparing a haloalkane comprising: (a) contacting a haloalkane starting material with a haloalkene starting material in the presence of an effective amount of a catalyst complex under conditions effective to facilitate an addition reaction and to form a product stream comprising a haloalkane product from said addition reaction, wherein said catalyst complex has a boiling point higher than that of said haloalkane product; and (b) recovering said haloalkane product from said product stream.

32 Claims, 1 Drawing Sheet

CONTINUOUS PROCESS FOR HCC-24/0f VERSION 1

CONTINUOUS PROCESS FOR HCC-24/0f VERSION 2

# CONTINUOUS PROCESS FOR MANUFACTURING HALOGENATED COMPOUNDS

FIELD OF INVENTION

Figure 1:
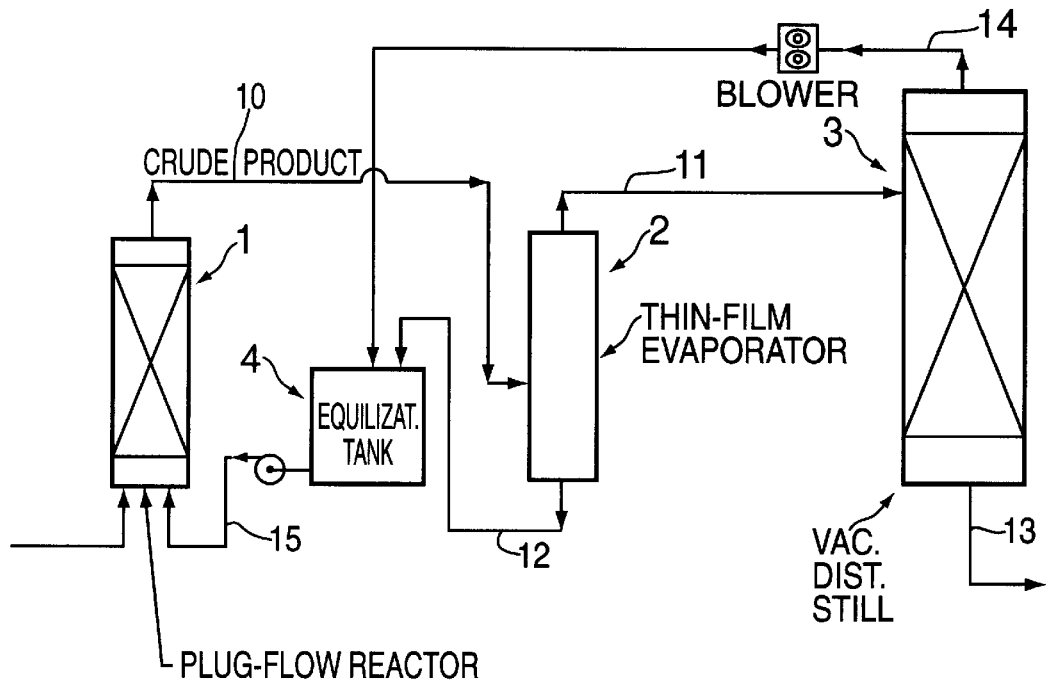

The present invention relates to a process for preparing halogenated alkanes. More specifically, the present invention relates to a continuous process for preparing halogenated compounds using an addition reaction.

BACKGROUND OF THE INVENTION

Addition reactions for preparing useful haloalkanes, such as 1,1,1,3,3-pentachloropropane (HCC-240) and 1,1,1,3,3-pentachlorobutane (HCC-360), are known in the art. Typically, in this reaction, a halogenated compound, such as, carbon tetrachloride, is added to an olefinic compound, such as, vinyl chloride, in the presence of a catalyst and under conditions sufficient to form a haloalkane product having a backbone longer than that of the haloalkane reactant. The halogenated product then is recovered by separating it from the reactants, catalyst and by-products using conventional techniques such as distillation.

Although widely used, this process suffers from several shortcomings, one of the more serious being that the process is not readily adapted to continuous operation. The problem is due, in large part, to the recovery of the halogenated product from the product stream. Often such recovery destroys the catalyst, thereby eliminating the ability to recycle the catalyst. For example, Kotota et al. "Addition of Tetrachloromethane to Halogenated Ethenes Catalyzed by Transition Metal Complexes". 77 J. Molec. Catal. 51–60 (1992), discloses a batch process for the preparation of HCC-240 from carbon tetrachloride and vinyl chloride using as a catalyst, cuprous salts, cuprous chloride and Cu[(CH$_3$—CN)$_4$]ClO$_4$, complexed with a cocatalyst, namely, n-butylamine. To recover the halogenated product, the catalyst and cocatalyst are removed by a water wash which destroys the catalyst. Since the catalyst is destroyed, it cannot be recycled. Reusing catalyst, however, is critical to a commercially-viable, continuous process.

Other recovery processes disrupt the preparation process, thereby complicating a continuous process or frustrating it altogether. For example, in conventional processes, where recovery is effected by distilling a product stream to separate the haloalkane from the reactants and catalyst, the more volatile cocatalysts tend to flash off thus leaving a solid catalyst in the distillation column. Eventually, the process must be interrupted and the catalyst removed from the column, filtered, and physically transported to another vessel where it is mixed with the cocatalyst and introduced back to the reaction. In addition to disrupting the process, these recovery steps add cost and complexity to the reaction process.

Aside from the shortcomings related to recovering the haloalkane product, convention addition reactions tend to have low selectivities. For example, Kotora et al., "Selective Additional of Polyhalogenated Compounds to Chlorosubstituted Ethenes Catalyzed by a Copper Complex," React. Kinet. Catal. Lett. 415–19 (1991) discloses batch preparation of HCC-240 from carbon tetrachloride and vinyl chloride using a cuprous chloride complex catalyst with 2-propylamine as a cocatalyst. The reported HCC-240 yield, however, is only 71%. Additionally, Zhiryukina et al. "Synthesis of Polychloroalkanes With Several Different Chlorine-Containing Groups," 1 Izv. Akad. Nauk SSR, Ser. Khim. 152–57 (1983) disclose also a batch process for preparing HCC-240 from carbon tetrachloride and vinyl chloride using a Fe(CO)$_5$-ethanol catalyst, which process reportedly yields 25% HFC-240. All of the above disclosed processes are disadvantageous in that they are batch processes of low productivity and they have low selectivity for HFC-240. The Zhiryukina et al. process is further disadvantageous because it uses a highly toxic catalyst.

Therefore, a need exists for an efficient and economical continuous process for producing haloalkane product in high yield. The present invention fulfills this need among others.

DESCRIPTION OF THE INVENTION AND PREFERRED EMBODIMENTS

The present invention provides a continuous, high-capacity process for the production of halogenated alkanes using a catalyst complex having a higher boiling point than that of the reaction product. Since its boiling point is higher, the catalyst complex is readily separated from the haloalkane product through distillation and may be recycled along with unused reactants. Furthermore, if its boiling point is sufficiently high or if it is immobilized on a nonvolatile substrate, the catalyst complex tends not to be vaporized during the reaction and remains in the reactor. With either approach, the haloalkane product is conveniently separated from the catalyst complex, thus minimizing disruptions to the process and promoting a continuous reaction.

One aspect of the invention is characterized by an addition reaction in which halogenated compounds are prepared using an effective amount of a catalyst complex having a boiling point above that of the halogenated compound. In a preferred embodiment, the process comprises: (a) contacting a haloalkane starting material with a haloalkene starting material in the presence of an effective amount of the catalyst complex under conditions effective to facilitate an addition reaction and to form a product stream comprising a haloalkane product from the addition reaction; and (b) recovering the haloalkane product from the product stream.

An important consideration in the process of the present invention is the catalyst complex which should have several properties/attributes. First, the catalyst complex must promote an addition reaction between the haloalkane and haloalkene starting materials. To this end, the catalyst complex should form either a homogeneous system in which the catalyst is miscible in the starting materials, or a heterogeneous solution in which just a portion of the catalyst complex is miscible in the starting material. The immiscible portion in a heterogeneous solution may be, for example, a solid substrate to which a catalytic organic ligand is anchored. Alternatively, the immiscible portion in a heterogeneous solution may be fine particles of catalyst.

Second, the catalyst complex must have a boiling point above that of the haloalkane product of the addition reaction. A significant difference in the boiling points is preferred to facilitate separation of the catalyst complex from the haloalkane product-the greater the difference, the more readily the two components can be separated. Preferably, the boiling point of the catalyst complex exceeds the boiling point of the haloalkane product by no less than about 10° C., and, more preferably by not less than about 20° C. Furthermore, it may be preferable to immobilize the catalyst complex on a non-volatile substrate to minimize the vaporization of the catalyst complex so that little or no catalyst complex is present in the product stream, and no post-reaction separation of the catalyst complex and the haloalkane product is required.

Third, the catalyst complex should be thermally stable, meaning that it does not thermally degrade during the addition reaction or in the post-reaction recovery stages. Preferably, the catalyst complex is stable up to about 90° C., and more preferably up to about 100° C.

It has been found that metallic catalysts and organic ligands form suitable catalyst complexes. As used herein, the term "metallic catalyst" refers to elemental powders, salts, and organometallic compounds of the transition metals. The preferred metallic catalysts include copper and iron. Exemplary cuprous salts and organometallic cuprous compounds include, without limitation, cuprous chloride, cuprous bromide, cuprous cyanide, cuprous sulfate, and cuprous phenyl. Exemplary iron salts and organometallic ferrous compounds include, without limitation, ferrous chloride, ferric chloride, Tris (2,2'-bipyridine) iron (II) hexafluorophosphate. Exemplary copper and iron powders preferably are fine, substantially pure powders having a particle size no greater than about 100 mesh, and preferably no greater than about 325 mesh. The more preferred metallic catalysts include cuprous chloride and iron powder.

The organic ligand should be capable of forming a complex with a metallic catalyst having the properties and attributes as described above. Suitable organic ligands include, amines, nitrites, amides, and phosphates.

More specifically, it has been found that primary and secondary amines having a backbone of four or more carbons tend to form a catalyst complex having the above-mentioned attributes. Examples of preferred amines include, for example, stearylamines, laurylamines, cyclohexylamines, octylamines, 2-ethylhexylamine, 2-octylamine, tert-octylamine, diaminododecane ($C_{12}H_{28}N_2$), hexamethylenediamine, and tetramethylenediamine. More preferred amines include, for example, cyclohexylamine, octylamine and tetramethylenediamine.

It has been found that nitrile groups having a backbone of three or more carbons tend to form catalyst complexes having the above-mentioned attributes. Examples of preferred nitrites include, for example, acetonitrile, pentanenitrile, benzonitrile, and tolunitriles. More preferred nitrites include, for example, acetonitrile and pentanenitrile.

It has been found that amides having a backbone of 2 or more carbons tend to form catalyst complexes having the above-mentioned attributes. Examples of preferred amides, for example, N-ethylacetamide, acetanilide, aceto-p-toluidide, and hexamethlyenephosphomamide. More preferred amides include, for example, hexamethylenephosphoramide.

It has been found that phosphates having a backbone of 3 or more carbons tend to form catalyst complexes having the above-mentioned attributes. Examples of preferred phosphates include, for example, trimethylphosphate, triethylphosphate, tributylphosphate, and triphenylphosphate. More preferred phosphates include, for example, tributylphosphate.

The choice of which specific organic ligand to use tends to depend on the catalyst used. Generally, although not limited by this theory, it has been found that amines and nitrites are particularly effective in forming suitable catalyst complexes with copper-containing catalysts; amides and phosphates are particularly effective in forming suitable catalyst complexes with iron-containing catalysts.

Particularly preferred combinations of catalysts and organic ligands are provided below in Table 1.

TABLE 1

Preferred Complexes

| Combination | Catalyst | Organic Ligand |
| --- | --- | --- |
| 1 | cuprous chloride | stearylamine |
| 2 | cuprous chloride | laurylamine |
| 3 | cuprous chloride | cyclohexylamine |
| 4 | cuprous chloride | octylamine |
| 5 | cuprous chloride | 2-ethylhexylamine |
| 6 | cuprous chloride | 2-octylamine |
| 7 | cuprous chloride | tert-octylamine |
| 8 | cuprous chloride | diaminododecane ($C_{12}H_{28}N_2$). |
| 9 | iron powder | tributylphosphate |
| 10 | iron powder | hexamethylenephosphoramide |
| 11 | iron powder | triphenylphosphate |
| 12 | ferric chloride | tributylphosphate |
| 13 | ferrous chloride | tributylphosphate |

The specific combination of catalyst and organic ligand used tends to depend upon their commercial availability, the reactants used, and the desired haloalkane product. For example, it has been found that, in the production of HCC-240 from vinyl chloride and carbon tetrachloride, the preferred catalyst complex is cuprous chloride-cyclohexyl amine, commercially available from Aldrich, Milwaukee, Wis., and, in the production of HCC-360 from 1,1,1-trichloroethane and vinylidene chloride the preferred catalyst complex is iron powder-hexamethylphosphoramide, commercially available from Aldrich, Milwaukee, Wis.

As mentioned above, the catalyst complex of the present invention also may include a solid/non-volatile substrate on which an organic ligand is immobilized. In other words, a solid/non-volatile substrate may be functionalized with an organic ligand such that the catalyst forms a miscible complex with the organic ligand functionality while the substrate remains immiscible. Since the catalyst complex is immobilized on a nonvolatile substrate it tends not to vaporize during the reaction, and, consequently, there is no need to separate the haloalkane product from the catalyst complex in post-reaction processing. Preferably, the substrate is an ion exchange resin having organic ligand functionality. Many such ion exchange resins are known. One example is Amberlite resin which contains amine functionality and is commercially available through Rohm & Haas (Philadelphia, Pa.).

Generally, the mole ratio of catalyst to organic ligand ranges from about 0.01:1 to about 50:1, and preferably from about 0.1:1 to about 3:1. For example, the mole ratio of cuprous chloride to cyclohexylamine is about 0.05:1 to about 2.0:1, preferably about 0.02:1 to 1.0:1, and, more preferably, about 0.1:1 to about 0.7:1. The mole ratio of iron powder to tributylphosphate may be about 0.05:1 to about 10.0:1, preferably about 1.0:1 to about 3.0:1, and more preferably about 1.5:1 to about 2.5:1.

The catalyst complex is used in an amount sufficient to catalyze the reaction of the haloalkane and haloalkene reactants. Preferably, the concentration of the catalyst in the reaction mixture ranges from about 0.01 to about 10 wt. %, preferably from about 1 to about 5 wt. %, and more preferably from about 1.5 to about 2.5 wt. %. For example, suitable results have been obtained using 1 wt. % of cuprous chloride cyclohexylamine to catalyze the reaction of carbon tetrachloride and vinyl chloride to form HCC-240.

The reactants used in the process of the present invention comprise a haloalkane and a haloalkene. A suitable haloalkane reactant in the process of the present invention has the following formula:

$$C_nH^mX^p \tag{1}$$

wherein:

n is an integer from 1 to 200, preferably from 1 to 20, and more preferably from 1 to 4;

each X is an independently selected halogen, preferably fluorine or chlorine, and more preferably chlorine; and m and p are integers selected from 0 to 2n+2 provided that m+p=2n+2.

Exemplary haloalkanes include, without limitation, carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane. Preferred haloalkanes include carbon tetrachloride, 1,1,1-trichloroethane, and 1,1,1-trichlorotrifluoroethane.

A suitable haloalkene reactant in the process of the present invention has the following general formula:

$$C_qH_rX_s \tag{2}$$

wherein:

q is an integer ranging from 2 to 200, preferably from 2 to 20, and more preferably from 2 to 4;

X is as described above with respect to Formula (1); and r and s are integers from 0 to 2q, provided that r+s=2q.

Exemplary haloalkenes include, without limitation vinyl chloride, 1,1-dichloroethene, trichloroethene, tetrachloroethene, chlorofluoroethene, 1,2-dichloroethene, 1,1-dichloro-difluoroethene, 1-chloro-1-propene, and 1-chloro-1-butene. Preferred haloalkenes include 1,1-dichlorodifluoroethene, 1,1-dichloroethene, and vinyl chloride.

The specific haloalkane and haloalkenes starting materials used depends in large part on their commercial availability and the desired haloalkane product. For example, to prepare HCC-240, the preferred reactants are carbon tetrachloride, available from Vulcan Chemicals (Birmingham, Ala.), and vinyl chloride, available from PPG Industries, (Pittsburgh, Pa.). To prepare HCC-360, the preferred reactants are 1,1,1-trichloroethane and 1,1-dichloroethene both available from PPG Industries.

The concentration of the haloalkane and haloalkene starting materials is determined by the desired haloalkane product and the stoicheometry of the addition reaction. Preferably, a stoichiometric excess of the haloalkane is used. The mole ratio of haloalkane to haloalkene is generally from about 1.2:1 to about 4:1, and preferably from about 1.5:1 to about 2.5:1.

The reactants are subjected to conditions sufficient to effect an addition reaction to produce a haloalkane product having a carbon chain longer than that of the haloalkane reactant. The haloalkane product has the following general formula:

$$C_uH_vX_w \tag{3}$$

wherein:

u is an integer greater than n as described above, and preferably n+q.

X is as described above with respect to Formula (1); and v and w are integers from 0 to 2u+2, providing that v+w=2u+2, preferably $2 \leq w \leq 2u+2$, and more preferably $3 \leq w \leq 2u$.

Exemplary haloalkane products include, without limitation, HCC-240, HCC-360, HCC-580 (heptachlorohexane).

To effect favorable selection and yields, it is preferable to achieve good mixing of at least a portion of the catalyst complex in the reactants. To this end, the catalyst may be added to the reactor containing the haloalkane, haloalkene and organic ligand, or the haloalkane and haloalkene may be added to a reactor containing the catalyst and organic ligand. Preferably, however, first the catalyst, organic ligand and haloalkane are mixed, then the mixture is degassed by quick partial evacuation of the vapors, and finally the haloalkene is added to the mixture.

The reaction should be conducted under operating conditions sufficient to effect the addition reaction of the haloalkane and the haloalkene in a continuous process. The specific reaction conditions are determined by the desired product, reactants and catalyst used. For example, in the preparation of HCC-240, suitable results have been obtained at temperatures from about 40° C. to about 180° C., and, preferably, from about 85° C. to about 110° C. Likewise, contact times tend to vary according to the catalyst used and the reaction conditions. For example, in the preparation of HCC-240, suitable results have been obtained with contact times from about 10 seconds to about 10 hours, and preferably from about 1 minute to about 5 hours. Furthermore, it has been found that agitation is helpful to increase contact between the reactants and the catalyst complex.

Reaction pressure typically is maintained by removing a product stream containing the haloalkane product from the reactor. Generally, the pressure should be maintained to achieve the desired contact times. It has been found that reaction pressures of about 1 psi to about 400 psi are preferred, while pressure of about 50 to about 200 psi are more preferred.

The reaction preferably is conducted continuously to produce a product stream containing halogenated product, plus volatile reactants and/or by-products. Depending on the catalyst system used, the product stream may also contain a portion of the catalyst complex. At this point, the product stream is subjected to conventional separation techniques and apparatus, such as distillation, to recover the halogenated compound. Traditionally, such recovery was complicated by the fact that the organic ligand tended to flash off during distillation leaving behind a solid catalyst in the distillation column. This would require interrupting the continuous process to remove the solid catalyst from the column.

The present invention, however, overcomes this problem by using a thermally-stable, high-boiling point catalyst complex as described above. The organic ligand in the catalyst complex of the present invention tends not to flash off and leave a solid residue behind. On the contrary, its high boiling point tends to facilitate recovery through distillation. Furthermore, in the case where a solid substrate is used, the catalyst complex is immobilized and thereby does not leave the reactor during the process. Thus, no separation is required.

In recovering the haloalkane product from the product stream, it is preferred to minimize the decomposition of the haloalkane product. That is, under high temperatures, the catalyst tends to react with the haloalkane product, thereby resulting in its decomposition. One approach to minimizing product decomposition is to minimize the contact time between the catalyst and the haloalkane product. In a preferred embodiment, this is accomplished by flashing off the haloalkane product along with the more volatile constituents of the product stream, leaving behind the less-volatile catalyst complex.

Alternatively or additionally, the haloalkane product may be "insulated" from the catalyst by chelating the catalyst with a chelating agent. Suitable chelating agents include, for example, organic phosphates, while tributylphosphate is preferred. Although the addition of a chelating agent is helpful in minimizing product decomposition, it nevertheless complicates the recovery of the haloalkane product by introducing another constituent to the process that eventually must be removed if the process is to be conducted continuously. Therefore, the use of a chelating agent may necessitate additional distillation steps.

The detrimental effect of introducing a chelating agent to the process can be obviated if the chelating agent is the same as the organic ligand used to form the catalyst complex. If the chelating agent is the same, there is no need to remove it, and, consequently, it can be recycled along with the catalyst complex back to the reactor.

Figure 2:
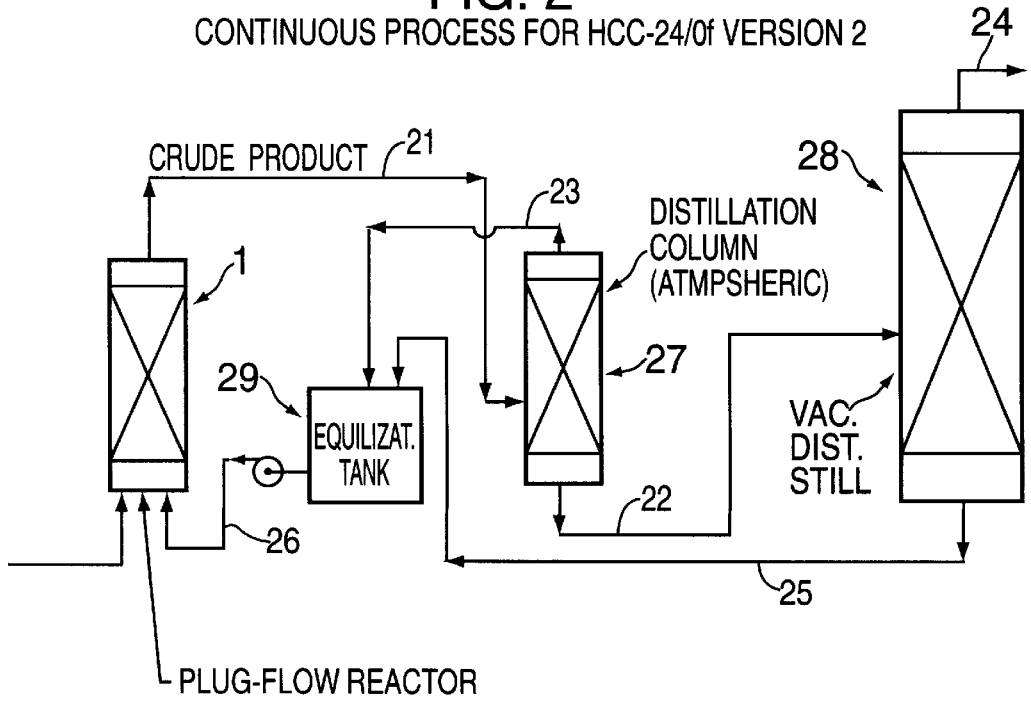

Preferred embodiments of systems for recovering the haloalkane product from the product stream are depicted, but not limited, schematically in FIGS. 1 and FIG. 2. In FIG. 1, the product stream 10 is continuously removed from a plug-flow reactor 1 (or a continuous stirred reactor). Product stream 10 is fed into a thin-film evaporator 2 where it is split into a top stream 11 and a bottom stream 12. The top stream 11 contains the haloalkane product along with more volatile compounds, such as the reactants, and the bottom stream 12 contains the catalyst complex.

Top stream 11 is fed to a distillation column 3 where it is further separated into a second top stream 14 and a second bottom stream 13. The second bottom stream 13 contains a purified form of the haloalkane product. This particular recovery scheme facilitates stripping the haloalkane product from the more volatile compounds.

The bottom stream 12 and the second top stream 14 optionally may be combined in an equalization tank 4 and recycled to the reactor 1 in recycle stream 15.

FIG. 2 shows an alternative embodiment of recovering the haloalkane product from the product stream. As shown, a product stream 21 is removed from a plug flow reactor 1 (or continuous stirred reactor), and is fed into a distillation column 27. Distillation column 27 is operated at conditions that separate product stream 21 into a top stream 23 containing volatile reactants, and a bottom stream 22. Bottom stream 22 contains the halogenated product and catalyst complex and is fed into vacuum distillation column 28. Vacuum distillation column 28 separates bottom stream 22 into a second bottom stream 25 containing the catalyst complex and a second top stream 24 containing a purified form of the halogenated product. As mentioned above, to minimize decomposition of the haloalkane product, an additional chelating agent may be used to chelate the catalyst. Preferably, the chelating agent is the same as the organic ligand to avoid the need for additional distillation steps to remove the chelating agent from the process.

The top stream 23 and the second bottom stream 25 optionally may be combined in an equalization tank 29 and then recycled to the reactor 1 in recycle stream 26.

What is claimed is:

1. A process for preparing a haloalkane comprising:
   (a) contacting a haloalkane starting material with a haloalkene starting material in the presence of an effective amount of a catalyst complex under conditions effective to facilitate an addition reaction and to form a product stream comprising a haloalkane product from said addition reaction, wherein said catalyst complex comprises a catalyst and an organic ligand selected from the group consisting of nitriles having a backbone of three or more carbons; amides having a backbone of two or more carbons; phosphates having a backbone of three or more carbons; primary amines selected from the group consisting of stearylamines, laurylamine, octylamine (liquid), 2-ethylhexylamine, 2-octylamine, tert-octylamine, diaminododecane ($C_{12}H_{28}N_2$), hexamethylenediamine, and tetramethylenediamine; and combinations of two or more thereof; and
   (b) recovering said halo alkane product from said product stream.

2. The process of claim 1, wherein the boiling point of said catalyst complex exceeds the boiling point of said haloalkane product by no less than about 20° C.

3. The process of claim 1, wherein said catalyst complex has a solid substrate.

4. The process of claim 1, wherein said catalyst complex is thermally stable up to about 90° C.

5. The process of claim 1, wherein said catalyst complex comprises a metallic catalyst and an organic ligand.

6. The method of claim 5, wherein said metallic catalyst is an elemental powder, salt, or organometallic compound of a transition metal.

7. The process of claim 6 wherein said catalyst complex is selected from the group consisting of a copper-containing catalyst/a primary amine; an iron-containing catalyst/an amide; an iron-containing catalyst/a phosphate and; a copper-containing catalyst/nitrile.

8. The process of claim 7, wherein said copper-containing catalyst is selected from the group consisting of cuprous chloride, cuprous bromide, cuprous cyanide, cuprous sulfate, and cuprous phenyl.

9. The process of claim 8, wherein said copper-containing catalyst is cuprous chloride and said primary amine is hexamethylenediamine.

10. The process of claim 7, wherein said iron-containing catalyst is selected from the group consisting of iron powder, iron ball, ferric chloride, ferrous chloride, and said organic ligand is selected from the group consisting of amides and phosphates.

11. The process of claim 10, wherein said iron-containing catalyst is iron powder and said amide is hexamethylene phosphoramide.

12. The process of claim 10, wherein said iron-containing catalyst is iron powder and said phosphate is tributylphosphate.

13. The process of claim 1, wherein the haloalkane is selected from the group consisting of carbon tetrachloride, 1,1,1-trichloroethane, dichlorofluoromethane, 1,1,1-trichlorotrifluoroethane, 1,1,2-trichlorotrifluoroethane, tetrachloroethane, pentachloroethane, and hexachloroethane; and wherein the haloalkene is selected from the group consisting of vinyl chloride, 1,1-dichloroethene, trichloroethene, tetrachloroethene, chlorofluoroethene, 1,2-dichloroethene, 1,1-dichloro-difluoroethene, 1-chloro-1-propene, and 1-chloro-1-butene.

14. The process of claim 13, wherein the haloalkane is selected from the group consisting of carbon tetrachloride, 1,1,1-trichloroethane, and 1,1,1-trichlorotrifluoroethane; and wherein the haloalkene is selected from the group consisting of 1,1-dichlorodifluoroethene, 1,1-dichloroethene, and vinyl chloride.

15. The process of claim 1, wherein said product stream comprises a portion of said catalyst complex; and step (b) comprises separating said catalyst complex from said haloalkane product through distillation; and said process further comprises:
   (c) recycling said catalyst complex.

16. The process of claim 15, wherein said catalyst is separated from said haloalkane product by flash distillation.

17. The process of claim 15, wherein said step (b) further comprises the step of introducing a chelating agent.

18. The process of claim 17, wherein said chelating agent is the same as said organic ligand.

19. The process of claim 1, wherein said product stream also comprises said catalyst complex and said haloalkane product is separated from said product stream by distilling the product stream into a top stream comprising said haloalkane product and a bottom stream comprising said catalyst complex.

20. The process of claim 19, further comprising distilling said top stream into a second top stream, which is recycled, and a second bottom stream comprising said haloalkane product.

21. The process of claim 1, further comprising distilling the product stream into a top stream comprising volatile reactants which are recycled, and a bottom stream comprising said catalyst complex and said haloalkane product; and further distilling said bottom stream into a second top stream comprising said haloalkane product and a second bottom stream comprising said catalyst complex which is recycled.

22. The process of claim 1 wherein the organic ligand is selected from the group consisting of nitriles having a backbone of three or more carbons; amides having a backbone of two or more carbons; phosphates having a backbone of three or more carbons; combinations of two or more thereof; and combinations of one or more thereof with a primary or secondary amine having a backbone of four or more carbon atoms.

23. The process of claim 22 wherein the organic ligand is a nitrile having a backbone of three or more carbons.

24. The process of claim 23 wherein the nitrile is selected from the group consisting of acetonitrile, pentanenitrile, benzonitrile, and tolunitriles.

25. The process of claim 24 wherein the nitrile is acetonitrile or pentanenitrile.

26. The process of claim 22 wherein the organic ligand is an amide having a backbone of two or more carbons.

27. The process of claim 26 wherein the organic ligand is N-ethylacetamide, acetanilide, aceto-p-toluidide and hexamethylenephosphoramide.

28. The process of claim 27 wherein the organic ligand is hexamethylenephosphoramide.

29. The process of claim 22 wherein the organic ligand is a phosphate having a backbone of three or more carbons.

30. The process of claim 29 wherein the organic ligand is trimethylphosphate, triethylphosphate, tributylphosphate and triphenylphosphate.

31. The process of claim 30 wherein the organic ligand is tributylphosphate.

32. The process of claim 22 wherein the organic ligand is a combination of two or more of nitrites having a backbone of three or more carbons; amides having a backbone of two or more carbons; phosphates having a backbone of three or more carbons; and primary or secondary amines having a backbone of four or more carbon atoms.

* * * * *

UNITED STATES PATENT AND TRADEMARK OFFICE
CERTIFICATE OF CORRECTION

PATENT NO. : 6,187,978 B1
DATED : February 13, 2001
INVENTOR(S) : Tedeusz P. Rygas and Hsueh Sung Tung It is certified that error appears in the above-identified patent and that said Letters Patent is hereby corrected as shown below:

<u>Title page,</u>
Item [75], Inventor, "Hsuch Sung Tung's" should be corrected to read -- Hsueh Sung Tung --.

Signed and Sealed this

Third Day of December, 2002

JAMES E. ROGAN
*Director of the United States Patent and Trademark Office*